(12) United States Patent
Windle

(10) Patent No.: US 6,223,687 B1
(45) Date of Patent: May 1, 2001

(54) HIGH EFFICIENCY VERMICULTURE PROCESS AND APPARATUS

(76) Inventor: Harry N. Windle, 12425 NW. Cr 231, Gainesville, FL (US) 32609

( * ) Notice: Subject to any disclaimer, the term of this patent is extended or adjusted under 35 U.S.C. 154(b) by 0 days.

(21) Appl. No.: 08/834,931

(22) Filed: Apr. 7, 1997

(51) Int. Cl.[7] .................................................. A01K 67/00
(52) U.S. Cl. ............................................................ 119/6.7
(58) Field of Search ................................. 119/6.7; 71/24

(56) References Cited

U.S. PATENT DOCUMENTS

| 4,187,946 | * | 2/1980 | Stevenson | 119/6.7 X |
| 4,262,633 | * | 4/1981 | Taboga | 119/6.7 |

FOREIGN PATENT DOCUMENTS

| 2615690 | * | 12/1988 | (FR) | 119/6.7 |
| 2151949 | * | 7/1985 | (GB) | 119/6.7 |

* cited by examiner

Primary Examiner—Robert P. Swiatek
(74) Attorney, Agent, or Firm—Sven W Hanson

(57) ABSTRACT

An apparatus and process for the efficient vermicomposting of organic containing wastes. A continuous thin layer of biomass is formed in which worms are established and encouraged to compost and migrate. The thinness of the biomass layer increases uniformity and allows for a higher rate of worm activity. By moving the biomass upon a conveying surface a continuous open system is created. New matter is introduced, digested and withdrawn while maintaining the active worms within a portion of the biomass. Spatial efficiency is provided by creating multiple beds in a stacked configuration.

20 Claims, 4 Drawing Sheets

HIGH EFFICIENCY VERMICULTURE PROCESS AND APPARATUS

BACKGROUND OF THE INVENTION

The present invention pertains to vermiculture and vermicomposting. In particular, the present invention provides a high efficiency process and apparatus for vermiculture and vermicomposting utilizing thin beds. Worm culture, or vermiculture, can provide worms as a raw material for an animal feed ingredient, live worms for sport fishing, or for other product uses. Vermicomposting is the use of worms to break down waste materials such as livestock manures and municipal waste. Generally, worms consume inorganic and organic matter, digest and absorb largely organic matter, and pass the remainder back to the soil. As a result of their feeding behavior, worms aid in the breaking down of organic material within the material they consume. The activity of worms also ventilates the soil and promotes bacterial and other microbial decomposition processes.

Large scale vermiculture typically uses thick beds in which large quantities of organic material are worked by worms in a relatively stationary mode. Thick beds typically become stratified with regions of active worms and regions of compacted material. These compacted regions often "sour" due to anaerobic decomposition resulting in unattractive conditions for worm activity. This requires turning or "freshening" of the beds such as by introduction of bedding materials. Thick bed operation is also typically a batch process requiring manual loading of fresh biomass. After the organic material is substantially broken down, the worms and digested material must be separated and harvested.

A need exists for a method of vermicomposting which provides: 1) uniform composting with lower labor demands; 2) better control of environmental conditions; 3) consistent and higher rates of worm activity with higher composting rates; 4) easier separation of worms from digested matter; and 5) an overall more predictable worm production and vermicomposting system for steady streams of waste. The present invention provides a unique process for high efficiency vermiculture and vermicomposting.

SUMMARY OF THE INVENTION

An object of the present invention is to provide a worm composting apparatus and process which utilizes thin beds to increase worm composting rates and improve uniformity of composting.

A second object of this invention is to provide a high efficiency worm composting apparatus and process which minimizes space requirements and maximizes the rate of decomposition.

Another object of this invention is to provide an improved method of worm composting requiring reduced labor over prior methods by eliminating the need for mixing.

Another object of this invention is to provide an improved worm culture apparatus that is inexpensive to construct and that is inexpensive to operate.

Yet another object of this invention is to provide a worm culture process which facilitates worm fecundity and provides excess worms as a product.

A further objective of the invention is to provide a worm composting apparatus and process having a stacked multi-bed configuration for increased spatial efficiency.

The present invention is a method by which composting and worm culture are improved by establishing thin layers of matter in which a high density worm mass is encouraged to actively move into and attack undigested material at high rates. The thinness of the layers encourages migration to other areas and results in decreased worm stratification and increased uniformity of composting. In order to facilitate the processing of large quantities of matter in this manner, the matter is formed into thin layers on a moving surface. By controlling the surface speed to match that of the worms migration through the layer of matter, a continuous process from a loading station to an unloading station can be maintained. The worms are always retained on the surface in a portion of the matter while the digested matter is removed. The organic-containing wastes treatable by this method and apparatus include diverse types of waste such as hog feedlot waste, dairy farm waste, presorted municipal waste, industrial sludges and other industrial process wastes, and food wastes.

The present thin layer vermiculture process produces a surplus worm population is produced over that required in the system for composting. Worm eggs and worms may be withdrawn to provide a product of the composting system. Alternatively, the worms and eggs may be reintroduced to increase worm numbers and efficiency.

In an example apparatus a continuous belt having a flat bed surface is provided on which an initial thin layer of organic material is introduced, and upon which the worms are allowed to establish themselves. The belt is set into motion while new organic matter is added at a loading station to maintain a continuous thin layer. At an unloading point composted matter is withdrawn. A control device maintains the belt motion. The matter to be composted is formed into layers having a thickness between 2 and 8 inches depending upon the nature of the waste material being treated. Such thin bed could be operated as a batch process, but the preferred method is to operate the belt continuously or semicontinuously. To provide the most efficient use of space, multiple beds are supported in a vertical stack. When these beds are also inclined a reduction of motive power is possible due to gravity forces drawing the loaded belts to the unloading station. Loading and unloading devices are provided for moving new material onto the belt and for removing digested material away from the belt. In one alternative, the digested material falls from the belt by gravity. Stacked beds allow incorporation of environmental controls by enclosing an arrangement of stacked beds within a boundary such as a warehouse or greenhouse. This or similar devices are used to maintain favorable temperatures and moisture content, and promote higher activity and digestion by the worms.

Higher efficiency may be obtained by providing incentives to keep the worms moving toward the new undigested material. Effective incentives are strong light and moving air at the unloading point at an end of the bed surface which encourages worms to move toward the loading point of the bed surface. The presence of new material at the loading point of the bed surface also encourages movement of the worms. Other incentives are electrical barriers and radiant heat devices.

In one configuration a continuous belt of a woven plastic sheet is used. It in turn is supported beneath by a bed pan of the same material. One advantage of such a construction is low cost which is particularly relevant in such locations as farms. These belts are slung between rollers of plastic or even wood, again allowing low cost. By inclining the beds, a single drive device connected to one roller of each worm bed in a stack can drive the entire assembly. Alternatively, independent drives may be employed.

These devices and processes may be used both with the objective of waste handling and as a means of producing worms as a product, or both simultaneously. Because of the uniform manner of composting, thin layer vermicomposting reduces the labor required as a means of waste processing. Because of the low space needs for such systems, environmental control allows for higher worm activity levels raising average composting rates. This is particularly advantageous in the northern climates where worms are otherwise dormant at ambient conditions much of the year.

The example embodiments provided are but a few illustrations of this novel vermicomposting invention. Other variations of the invention will be obvious to those skilled in the art of vermicomposting and vermiculture.

DESCRIPTION OF THE PREFERRED EMBODIMENTS

The present invention is an apparatus and process for composting organic wastes in a highly efficient manner. In particular, the invention utilizes the great capacity of vermicomposting. The term "vermicomposting" as used here is understood to be the breakdown of organic matter by the ingestion and digestion of the matter by worms. As well, vermicomposting also includes the collateral biotransformation of such organic matter from the bacterial action inherent in such systems. The present invention has the capacity to cultivate a large number of worms—as excess over that needed for composting purpose. As such the present invention is also an apparatus and process for worm production. There is believed to be at least hundreds of species of what are commonly known as "red" worms in the vermicomposting technology. One example being the Lumbricus rubellus. Generally, species of red worm are regarded equally in vermicomposting and while the red worm is the type used to demonstrate the present invention, other types will work equally, depending somewhat upon the type of organic matter and environment.

The present vermicomposting invention utilizes a relatively thin bed, or layer, of organic matter in which the worm mass does its job. This process can be effectively used to transform or compost any number of waste materials such as restaurant food wastes; farmyard wastes such as chicken, pig, or bovine manure; vegetation; crop residues; sewage solids and similar organic-containing wastes. The organic-containing matter is collected, possibly pretreated, and then formed into a thin layer biomass. Pretreating may consist of grinding to reduce size and increase homogeneity and inoculation with beneficial bacteria. Biomass as used here means the general flow of organic-containing matter as it is introduced to the worms, the partially digested organic-containing matter infiltrated with worms, as well as the worm castings and undigested organic-containing matter that flows from the worm mass as vermicomposting.

In order to create a highly efficient vermicomposting system it is necessary to create a biomass is which worm mass stratification is minimized and where worm movement into undigested material is encouraged. A principal step in accomplishing this is to form a sufficiently thin biomass layer. Typically, where thick beds are used for vermicomposting—for instance beds 2 to 5 feet thick—worm mass stratification results in areas of high worm density along with areas of compacted matter. When a sufficiently thin biomass layer is provided and introduced to a worm mass, the worms will move more uniformly through the biomass creating an uniformly digested compost. How this may be done in a efficient and effective way is provided below.

Figure 1:
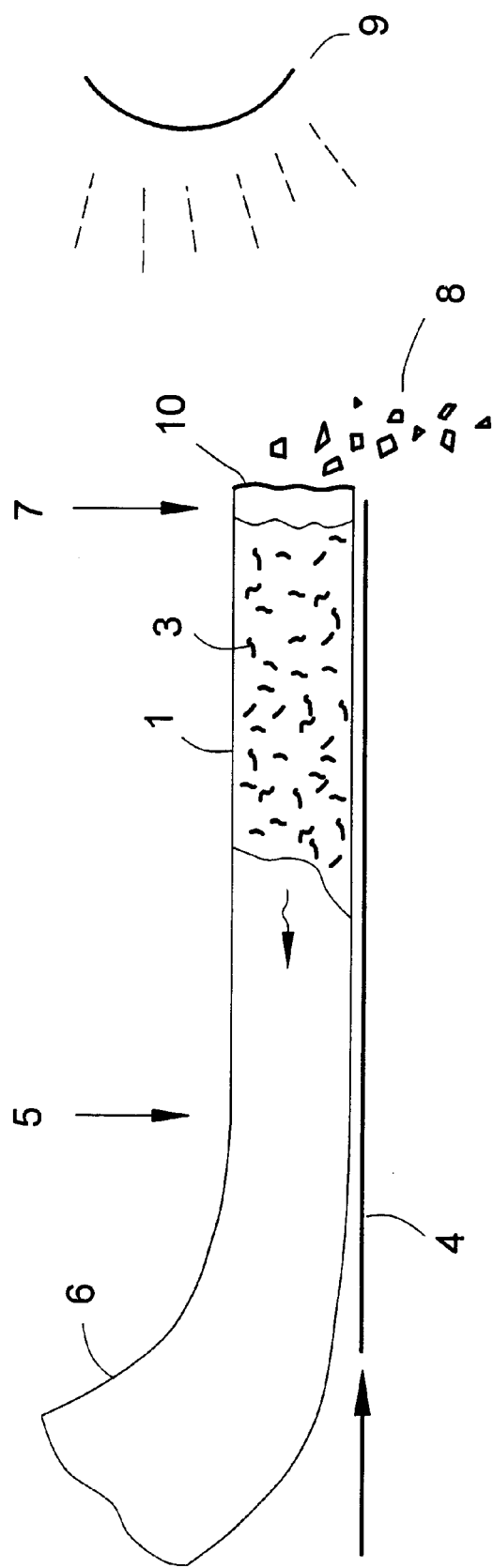
FIG. 1 is a diagram of a vermicomposting process using a thin layer biomass.

FIG. 1 is a functional diagram of a thin layer biomass vermicomposting system. An active portion 1 of the biomass is infiltrated with worms 3 effectively through its entire thickness. The vertical thickness of the biomass is from 2 (two) inches to 8 (eight) inches. When the biomass is cow manure the preferred thickness is about 4 (four) inches. Greater thickness may result in stratification of the worm mass or regions of the biomass which are bypassed by the worm mass. The term "worm mass" is used to indicate the collective worms active within the biomass. While a stationary bed may be used in thin layer vermicomposting, problems exist with loading and unloading of the biomass and separation of the worms from the digested biomass. What is preferred is to provide a conveying device having a moving bed surface 4 which slowly moves the thin layer from a loading point 5 at which the thin layer is formed from newly introduced undigested biomass 6, to an unloading point 7 at which the digested biomass 8 is withdrawn. As the worms consume the limited food supply in the thin layer they are forced to travel toward the undigested biomass. In the figure, the worm motion is from right to left. If the speed of the bed surface 4 movement matches, in the opposite direction, that of the worms, the worms will be held respectively stationary while a digested portion of the biomass is withdrawn, substantially free of worms. The digested biomass 8 is shown crumbling and falling, by gravity, off the end of the biomass layer as it reaches the unloading point at an end of the bed surface and the biomass is no longer supported from beneath. Because the worms will naturally avoid the free surface 10, the portion of the biomass exposed is generally free of worms. A worm incentive device, in this case a light source 9 such as fluorescent light may also be employed. The function of the incentive device is to drive the worm from the digested biomass and deeper into the undigested biomass. The presence of the light source 9 will drive the worms deeper into the biomass making it easier to withdraw the digested portion free of worms. Other incentives include moving air, electrical currents, radiant heat, and vibration directed at the exposed surface 10. A fan blowing air on the exposed surface 10 also will encourage worms deeper into the biomass. Withdrawal of the digested biomass can be effected by other means as well, such as mechanical devices able to remove small portions of the biomass at a time. Of course, the speed of the worms within the biomass is dependent on many factors including the nature of the biomass and the environmental conditions. Worm activity is particularly dependent on temperature. In order that the worms are enabled to travel through all portions of the thin layer biomass, it is necessary that the biomass be loaded at a rate to form a substantially contiguous layer. If breaks, interruptions or islands occur, the worms will be either cut off or greatly slowed. The function of the conveying device and bed surface may be satisfied by many different structures. In addition to those shown in the following examples, other structures which provide the same function of moving and maintaining a contiguous thin layer of the particular biomass in a manner controllable to the rate of worm motion may be employed. Although in FIG. 1, the surface bed is shown horizontal and flat other configurations are employed as well.

Figures 2A, 2B:
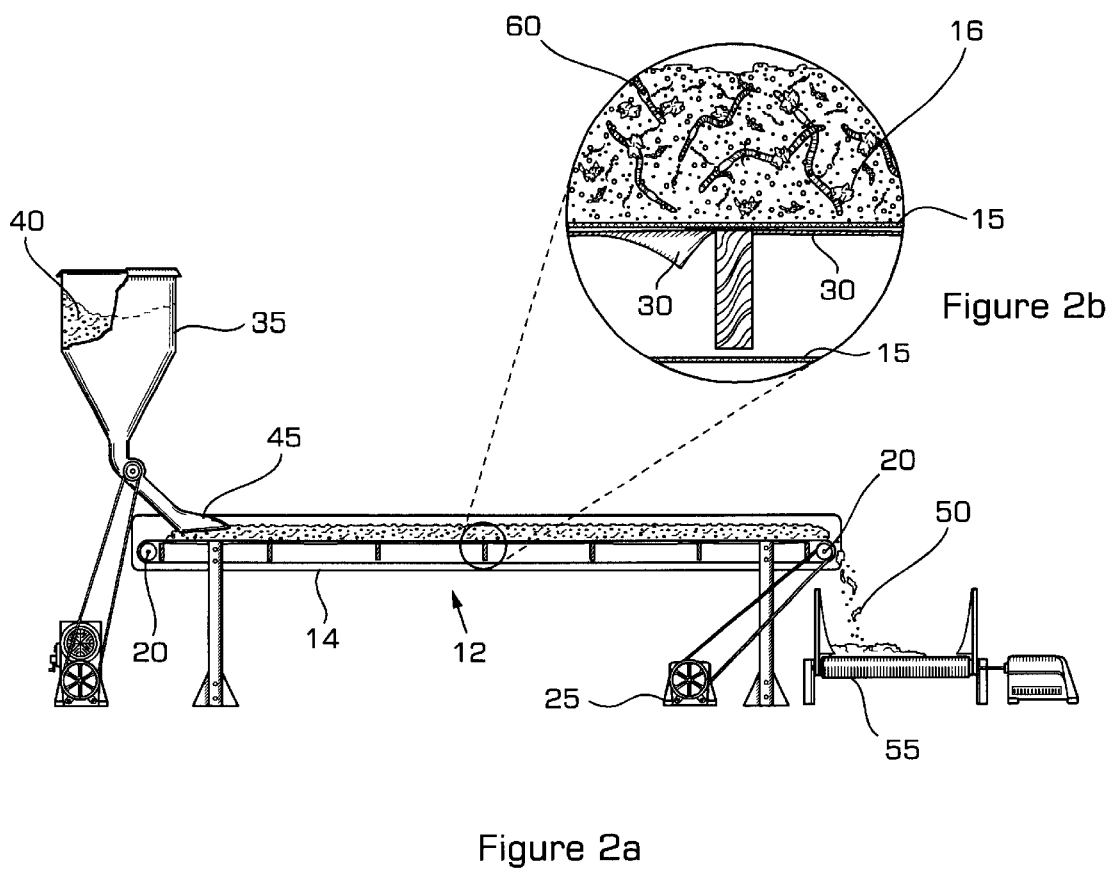
FIGS. 2a and 2b depict one embodiment of the invention using a single horizontal bed.

In FIGS. 2a and 2b, an example apparatus is shown for establishing a thin layer biomass. A conveying device 12 is shown in cross-section. This horizontal conveying device includes a support structure 14 on which is supported a continuous loop belt 15. The belt loops over rollers 20 at both ends of the support structure thereby allowing motion. A drive mechanism 25 such as an electrical motor is linked to the rollers or to other drive devices for moving the belt. A drive mechanism for extremely low speeds is required to provide the low linear belt speeds necessary in this device. A stepper motor with reduction or similar mechanisms well known in the arts may be used to obtain these low speeds. Some typical conveyor speeds are given in the example below. A bed pan 30 is provided secured rigidly to the support structure to form a foundation supporting the belt. In this configuration, the bed pan 30 is a fabric stretched between the individual members of the support structure 14. The width of the entire assembly is arbitrary and is determined from the particulars of the site. In operation, a feed hopper or trough 35 is filled with undigested biomass 40 which is then introduced onto the belt 15. The belt provides a bed surface 16 on which the biomass remains as it is composted. A leveler 45 is provided as necessary to provide an even distribution and thickness. Alternatively, a gate or weir may be provided the appropriate distance above the belt at the loading point. The biomass is then effectively extruded onto the belt by forcing the biomass between the belt and gate, the gate regulating the thickness of the layer. The belt 15 is driven at a speed which closely matches the worm mass progression through the thin layer biomass. The digested biomass 50 falls from the belt and is withdrawn from the site by a second conveyor 55. In the expanded view, the thin layer biomass is shown infiltrated by worms 60. While the various elements such as the feed hopper and conveyor may be structurally connected they may also be only functionally connected by being located in sufficient proximity and in proper orientation to function effectively together.

Figure 3:
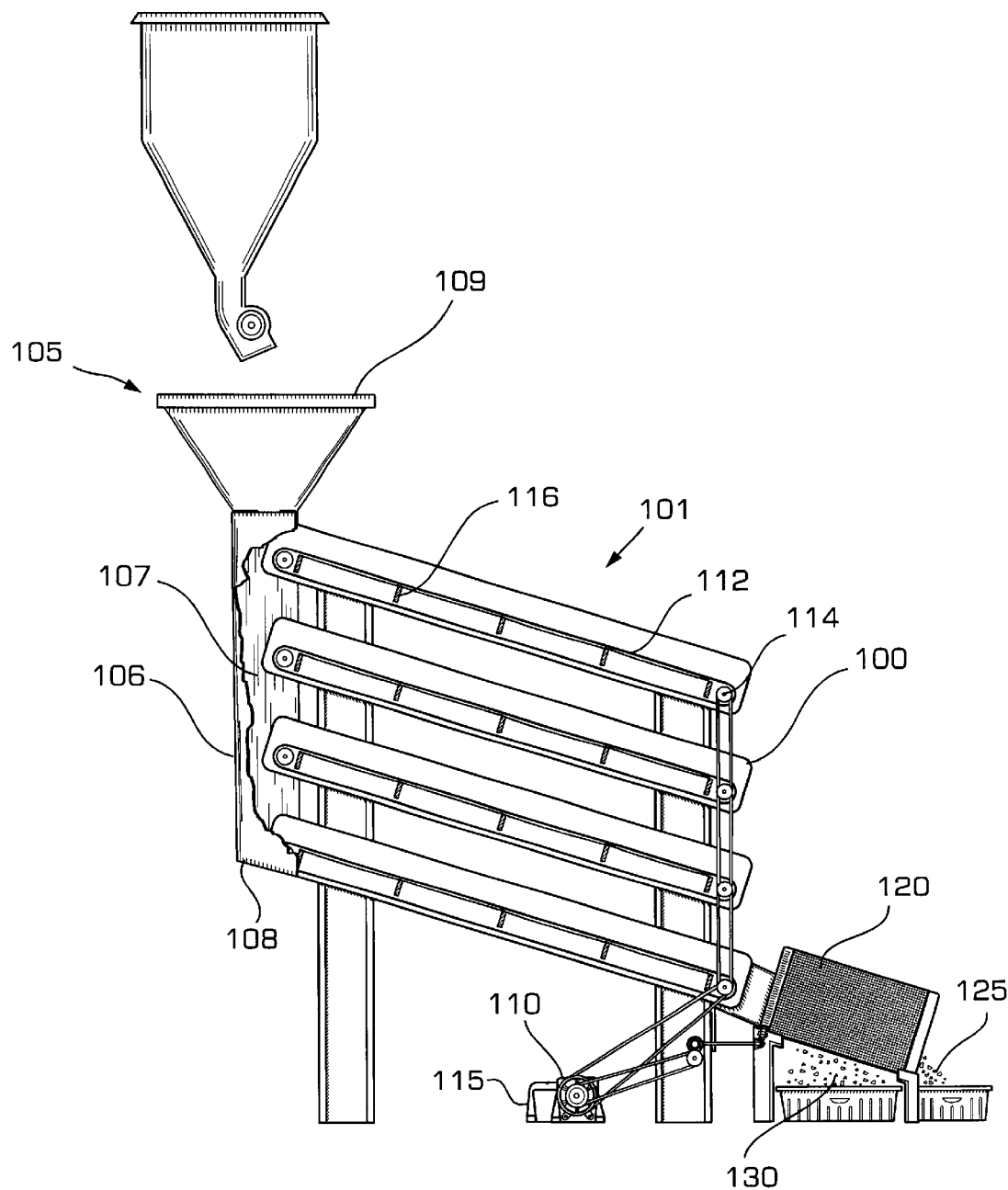
FIG. 3 is an embodiment of the invention having multiple beds in a vertical stacked configuration.

An example of a space and cost effective design for implementing the invention is shown in FIG. 3. Multiple inclined conveyors 100 are supported in a vertically stacked configuration to form a conveyor assembly 101. Each conveyor includes a loop conveyor belt 112 which is captured between rollers 114 as similarly described. A support structure 116 is provided to support the weight of the loaded belts. The top surface of each belt 112 forms bed surface which is loaded with undigested biomass by means of a single box feeder 105. The feeder box is formed of a broad back 106 which spans the full width of the conveyor belts 100. Sides 107 and a bottom 108 extend toward the conveyor belts and capture the biomass introduced. The near side of the feeder box 105 is cut away in the view to expose the conveyor loading ends. The fourth, open, side of the feeder box is effectively filled by the loading ends of the conveyors. The sides 107 are snug to the conveyor sides to reduce leakage. Biomass to be loaded is introduced into the feeder box mouth 109 and allowed to accumulate in the box. The weight of the biomass will force it to flow between the individual conveyors and onto the belts 112. The gap between rollers at the loaded end of the conveyors determines the thickness of the biomass layer formed. This spacing is exaggerated in the figure for clarity. Other devices and methods for loading such a material stream onto a conveying surface are within the knowledge of those skilled in materials transportation. Each conveyor 100 is inclined at a downward angle from the loading end to the unloading end as shown. Because the weight of the biomass on the bed surfaces may be extreme, the frictional resistance to belt movement may be great. The incline allows the weight of the biomass drawing the belt down to counter the frictional forces and reduce the motor power required to drive the belts. The exact angle is dependent on the construction materials and the density of the biomass. The belt material and bed pan material greatly influence the friction forces as the contact surface area is great. A reduced speed drive 110 similar to that in the previous figure is provided, linked either directly or indirectly to each belt. A speed and timing control 115 is provided on the drive 110. These components are but one way in which the belt motion may be controlled. Alternative methods such as independent drives for each belt are also available. While motion of the conveyor belts and bed surfaces has been discussed as continuous, noncontinuous motion will also be satisfactory. Short duration motions with long intervening stationary periods will effect the same result so long as the motions are short enough that large portions of the digested biomass are not withdrawn at a single time carrying along worms.

A screen tumbler 120 is shown, for convenience, placed at the unloading end of the conveyor assembly 101 such that digested biomass will fall into the open end of tumbler. The function of the screen tumbler is to separate the larger undigested lumps of biomass 125, and incidental worms, from the more fine worm castings material 130 which has been digested. The screen size is again dependent upon the particular biomass. For cow manure vermicomposting, a ⅛ inch screen followed by a ¼ inch screen has been found to work well. Preferably, all but the material passing through the ⅛ inch screen is returned to the undigested biomass to be reloaded and form the thin layer. It has been found that in this manner a large quantity of worm egg casings will be returned to hatch within the worm mass thereby supporting the worm population. Alternatively, the egg casing containing portion may be removed to allow for incubation of the worm eggs and production of worms.

EXAMPLE

A vertically stacked vermicomposting assembly was built having 7 individual inclined thin layer biomass beds. The beds were each inclined at an included angle of 24 degrees from the horizontal—the output end being lower. The assembly sides were covered with a polyethylene sheet to help maintain an elevated temperature. A supply of cow manure was liquefied, pumped into a hopper, and then allowed to gravity drain for 24 hours after which it was hand loaded into a gravity feed trough loading simultaneously all of the beds. The trough enclosed the loading end of the beds and the weight of a height of biomass above the beds forced a portion of the biomass from the trough, through a slot, onto each bed surface. Between vertically adjacent beds, this slot was formed by the space between the respective bed rollers. The device was similar to that shown in FIG. 3. A supply of red worms was obtained, distributed onto the beds, and briefly allowed to become established. The beds were put into motion and additional biomass was loaded maintaining a continuous thin layer on the beds. Both a simple electrical fan and two 40 watt fluorescent light bulbs were directed at the unloading end of the assembly as incentives. The digested biomass was withdrawn by gravity drawing the overhanging portion of the thin layers to fall from the beds into trays. The digested biomass was then screened through an 1/8 inch wire mesh and the residual returned to the feed trough. The residual consisted primarily of small lumps of undigested manure, worms, and worm egg casings clinging to the undigested manure. Approximately one third of the volume of material withdrawn from the beds was returned to the biomass to be loaded. The assembly was operated exposed to ambient conditions that ranged from about 40 degrees (F) at initiation to 78 degrees (F) after several weeks. As a consequence, the worm activity rate increased such that the bed surface movement was accelerated. The parameters and results of the example process are provided in the following table.

TABLE 1

Example Process Parameters

| | |
|---|---|
| Biomass | Cow Manure |
| Moisture content | Gravity drain 1 day |
| red worms initially introduced | approx. 1 lb./ft$^2$ |
| Number of bed surfaces | 7 |
| Angle of incline | 24 degrees |
| Individual bed length | 9 feet |
| Individual bed width | 6 feet |
| Vertical spacing | 10 inches on center |
| Bed fabrication | Woven plastic fabric |
| Bed pan material | Woven plastic fabric |
| Approximate biomass thickness | 4 inches |
| Ambient Temperature | 40–78 degrees |
| Linear speed of bed surface | 1 to 1.5 ft./day |
| Incentives | Air motion and light |
| Calculated net compost rate | 10 to 14 cu.ft./day |

The example apparatus was constructed similar to that shown FIG. 3. A support structure was formed of wood members and wood rollers were also utilized. The woven plastic fabric belt was connected to the rollers solely by friction. The effectiveness of this inexpensive apparatus demonstrates the potential low cost of this design and process. Over the course of operation of this prototype the worm density was found to have increased greatly. A consequence of the continuous movement the worms live in a continuously refreshed biomass as compared with static or thick beds. The result of this continuous process is a high rate of waste decomposition.

Figure 4:
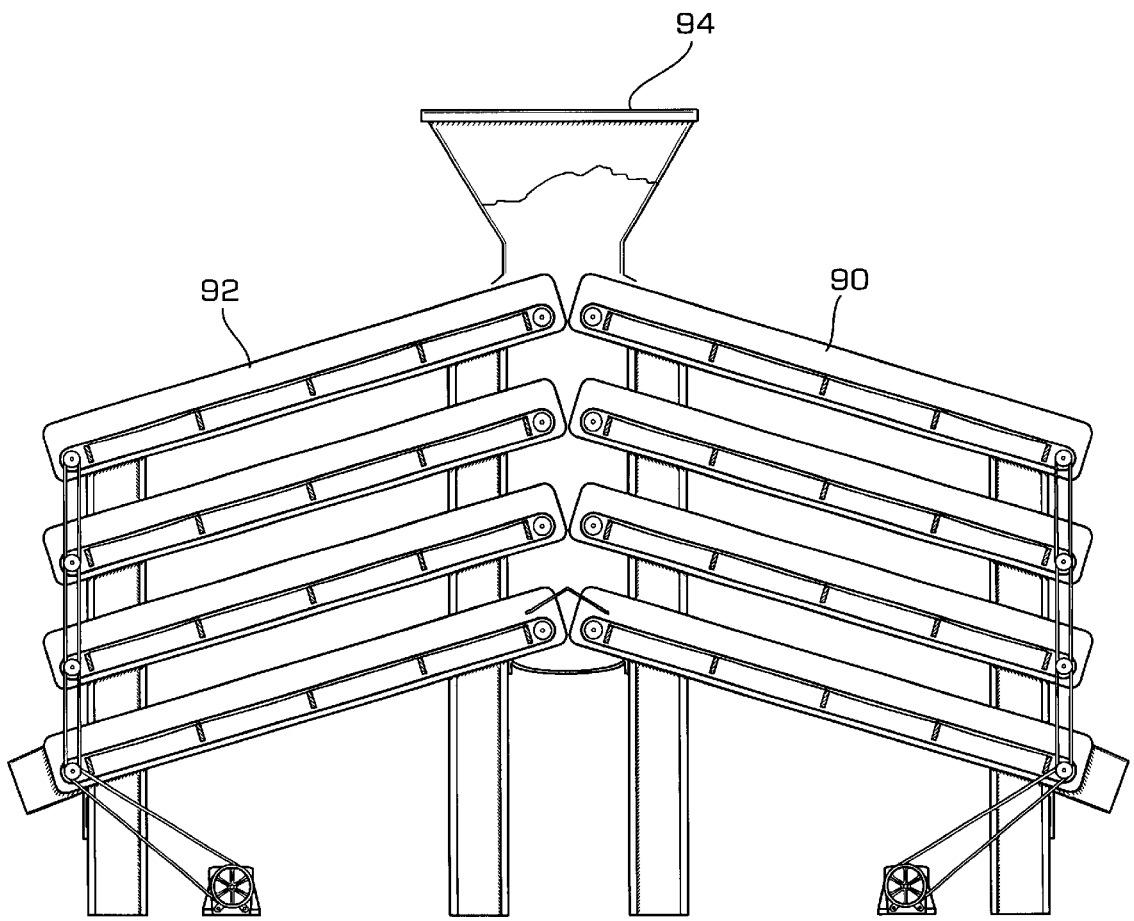
FIG. 4 is an alternative configuration in which two stacked bed assemblies are arranged back-to-back to facilitate loading.

FIG. 4 depicts an alternative configuration having two bed stacks 90 and 92. These are arranged such that the loading end of each is directed toward a common feed trough 94 which functions as a loading device. The beds operate similarly to those described in FIG. 3. Undigested biomass is introduced into the feed trough at the top. Gravity drives the biomass onto the bed surface. The near side of the trough is removed in the view to expose the individual conveyor loading ends. As explained in the example above, the biomass is driven onto all but the top-most bed through the gap between the adjacent bed rollers. The bed-to-bed vertical spacing as well as the roller diameter will determine the thickness of the biomass layer. Alternatively, the trough structure could include tapered or funnel slots opening onto the bed surfaces to ease flow. This arrangement provides a simple method of loading while improving space efficiency.

While the preceding examples are provided to demonstrate implementation of the claimed invention, the scope of the invention is not limited to these. It will become obvious to those skilled in the art to incorporate existing and future materials and devices into other embodiments of the invention.

I claim:

1. A high efficiency vermiculture apparatus which reduces stratification of worms in the biomass being composted and increases worm density and efficacy, the apparatus comprising:

a thin layer biomass, said thin layer biomass having a thickness in the range of about 2 to 8 inches;

a worm mass within said thin layer biomass;

an input end and an output end;

a conveyor means for conveying the thin layer biomass from the input end to the output end: such that the thin layer biomass may be digested by the worm mass as the thin layer biomass is conveyed from the input end to the output end.

2. The vermiculture apparatus of claim 1 wherein:

said thin layer biomass has a thickness of about 4 inches.

3. The vermiculture apparatus of claim 1;

wherein the conveyor means comprises a movable first bed surface; and said apparatus further comprising:

a control means for controlling the movement of said first bed surface; said control means being functionally connected to said first bed surface;

such that said thin layer biomass remains on the first bed surface for sufficient time for the thin layer biomass to be appreciably digested before reaching the output end.

4. The vermiculture apparatus of claim 3;

further comprising a feeder for feeding undigested biomass in a distributed manner on the first bed surface;

said feeder being functionally connected to said first bed surface and to said control means;

such that the biomass may be fed in a substantially continuous thin layer on the first bed surface.

5. The vermiculture apparatus of claim 3, further comprising:

a first continuous flexible belt; said flexible belt having a surface forming said first bed surface.

6. The vermiculture apparatus of claim 5 wherein:

said first belt is aligned at a substantial included angle from the horizontal.

7. The vermiculture apparatus of claim 6 wherein:

said first belt is aligned at an included angle of about 24 degrees from the horizontal.

8. A high efficiency vermiculture apparatus which reduces stratification of worms in the biomass being composted and increases worm density and efficacy, the apparatus comprising:

a thin layer biomass, said thin layer biomass being capable of sustaining an infiltrated worm mass;

an input end and an output end;

a conveyor means for conveying the thin layer biomass from the input end to the output end said conveyor means comprising:

a movable first bed surface; and a plurality of elevated bed surfaces; and a control means for controlling the movement of said first bed surface; said control means being functionally connected to said first bed surface and to each of said elevated bed surfaces;

a support structure; each of said elevated bed surfaces being supported by said support structure a predetermined vertical distance above said first bed surface; forming a stacked configuration;

such that said thin layer biomass remains on the bed surfaces for sufficient time for the thin layer biomass to be appreciably digested before reaching the output end.

9. The vermiculture apparatus of claim 8; further comprising:

at least one worm motion incentive; said incentive being functionally associated with said conveyor means at said output end.

10. The vermiculture apparatus of claim 9 wherein:

said incentive is a light emitting device.

11. A high efficiency vermiculture apparatus which reduces stratification of worms in the biomass being composted and increases worm density and efficacy, the apparatus comprising:

a. a plurality of conveyors, each of said conveyors comprising:

1. a movable continuous loop belt, said belt being formed of a woven fabric, and each belt having a bed surface;

2. a pair of separated rollers, said belt being supported around said rollers;

3. a bed pan; said bed pan being formed of a woven fabric and being fixedly disposed beneath said belt; and b. a support structure, said support structure being formed of wood members, each of said conveyors being supported in an inclined orientation by said structure in a vertically stacked configuration;

c. a drive motor connected to at least one of each pair of said rollers; and d. a control device functionally connected to said drive mechanism;

e. a thin layer biomass formed on at least one of the bed surfaces; said thin layer biomass being capable of sustaining an infiltrated worm mass.

12. The vermiculture apparatus of claim 11, further comprising:

a. a second support structure;

b. a second plurality of conveyors, each of said second plurality of conveyors being supported in an inclined orientation by said second support structure in a vertically stacked configuration;

c. both of said support structures being relatively located to form a space between the first and second plurality of conveyors; and d. a loading trough formed around and at least partially enclosing said space; such that in operation additional biomass may be placed into the feeding trough and thereby be loaded onto said bed surfaces.

13. A high efficiency vermiculture process in which a worm mass is moved through a biomass layer such as to digest the biomass in complete and thorough manner to form a more uniform compost, the process comprising the steps of:

establishing a worm mass within a biomass;

introducing undigested biomass in a distributed, substantially continuous manner, creating a substantially continuous thin layer in communication with the worm mass;

retaining said thin layer in a substantially continuous manner such that the undigested biomass may be infiltrated by the worm mass and is thereby appreciably digested;

moving the thin layer to allow the effectively continuous introduction of new undigested biomass; and withdrawing the digested biomass such as to create an exposed biomass surface while retaining the worm mass in communication with the undigested biomass;

such that a continuous open process is provided whereby a continuous flow of undigested biomass may be infiltrated and digested by worm mass moving through the stream.

14. The vermiculture process of claim 13 further comprising:

encouraging the worms to move toward the undigested biomass by providing an incentive.

15. The vermiculture process of claim 14, further comprising:

enclosing the thin layer; and controlling the environmental conditions so as to encourage digestion and bacterial decomposition of the biomass.

16. The vermiculture process of claim 13, wherein:

repeating the previous steps thereby providing a plurality of thin layers in close proximity.

17. The vermiculture process of claim 16, further comprising;

screening the withdrawn digested biomass to separate a portion of the biomass; and introducing the separated portion to the undigested biomass to form the continuous thin layer.

18. A high efficiency vermiculture process in which a worm mass is moved through a biomass layer such as to digest the biomass in complete and thorough manner to form a more uniform compost, the process comprising the steps of:

a. forming a thin layer biomass;

b. establishing a worm mass in a portion of the biomass;

c. allowing the worm mass to migrate into an undigested portion of the biomass;

d. moving the biomass at an average linear speed effectively equal to, and opposite in direction to, the worm mass migration through the biomass; and e. withdrawing the digested biomass, such that the worm mass is retained in substantially one location.

19. The vermiculture process of claim 18, wherein:

the step of moving the biomass comprises moving the biomass in a series of alternating movements and rests having an combined average linear speed effectively equal to, and opposite in direction to, the worm mass migration through the biomass.

20. The vermiculture process of claim 19, further comprising:

reintroducing and intermixing a portion of the withdrawn digested biomass into the thin layer biomass such that the worm mass is provided a mixture including previously digested biomass.

\* \* \* \* \*